United States Patent [19]

Wall

[11] Patent Number: 4,781,687
[45] Date of Patent: Nov. 1, 1988

[54] IRRIGATION SYSTEM UTILIZING AIR BLADDER PRESSURE REGULATOR AND METHOD OF USE

[75] Inventor: R. E. Wall, Laguna Hills, Calif.

[73] Assignee: Baxter Travenol Laboratories, Inc., Deerfield, Ill.

[21] Appl. No.: 920,043

[22] Filed: Oct. 16, 1986

[51] Int. Cl.$^4$ .............................................. A61M 1/00
[52] U.S. Cl. .................... 604/118; 604/141; 604/153; 604/54; 251/5
[58] Field of Search .............. 128/DIG. 3, DIG. 25; 604/31–33, 6, 30–34, 36, 37, 118, 141, 142, 151–153, 250, 54, 6; 251/5

[56] References Cited

U.S. PATENT DOCUMENTS

| | | | |
|---|---|---|---|
| 2,568,566 | 9/1951 | Sokolik | 604/35 |
| 2,734,526 | 2/1956 | Aagaard | 251/5 |
| 3,039,733 | 6/1962 | Mattioli | 251/5 |
| 3,538,917 | 11/1970 | Selker | 251/5 |
| 4,604,089 | 8/1986 | Santangelo et al. | 604/30 |
| 4,650,462 | 3/1987 | DeSatnick et al. | 604/30 |

Primary Examiner—John D. Yasko
Assistant Examiner—J. L. Kruter
Attorney, Agent, or Firm—Tilton, Fallon, Lungmus & Chestnut

[57] ABSTRACT

A pressure regulation device utilized in an irrigation system. The pressure regulation device includes an inflatable air bladder within a housing in which a flow-through egress bladder connected to the irrigation site is placed. An operator may inflate the air bladder which is in contact with the egress bladder to restrict the flow of irrigation fluid to thereby increase the fluid pressure at the irrigation site such as a joint capsule. Once the fluid pressure in the egress bladder displaces air in the air bladder an equilibrium is reached between the air pressure in the air bladder and fluid pressure in the egress bladder and joint capsule. The operator may control the fluid pressure in the joint capsule by controlling the air pressure in the air bladder. To reduce pressure at the irrigation site, the operator deflates the air bladder to allow for increased fluid flow through the egress bladder. Further, a method of regulating the pressure in an irrigation system and an irrigation system including a pump, catheters for providing access to and egress from the irrigation site and a pressure regulation apparatus in communication with a line from the egress catheter, all connected in series with one another, are disclosed.

16 Claims, 3 Drawing Sheets

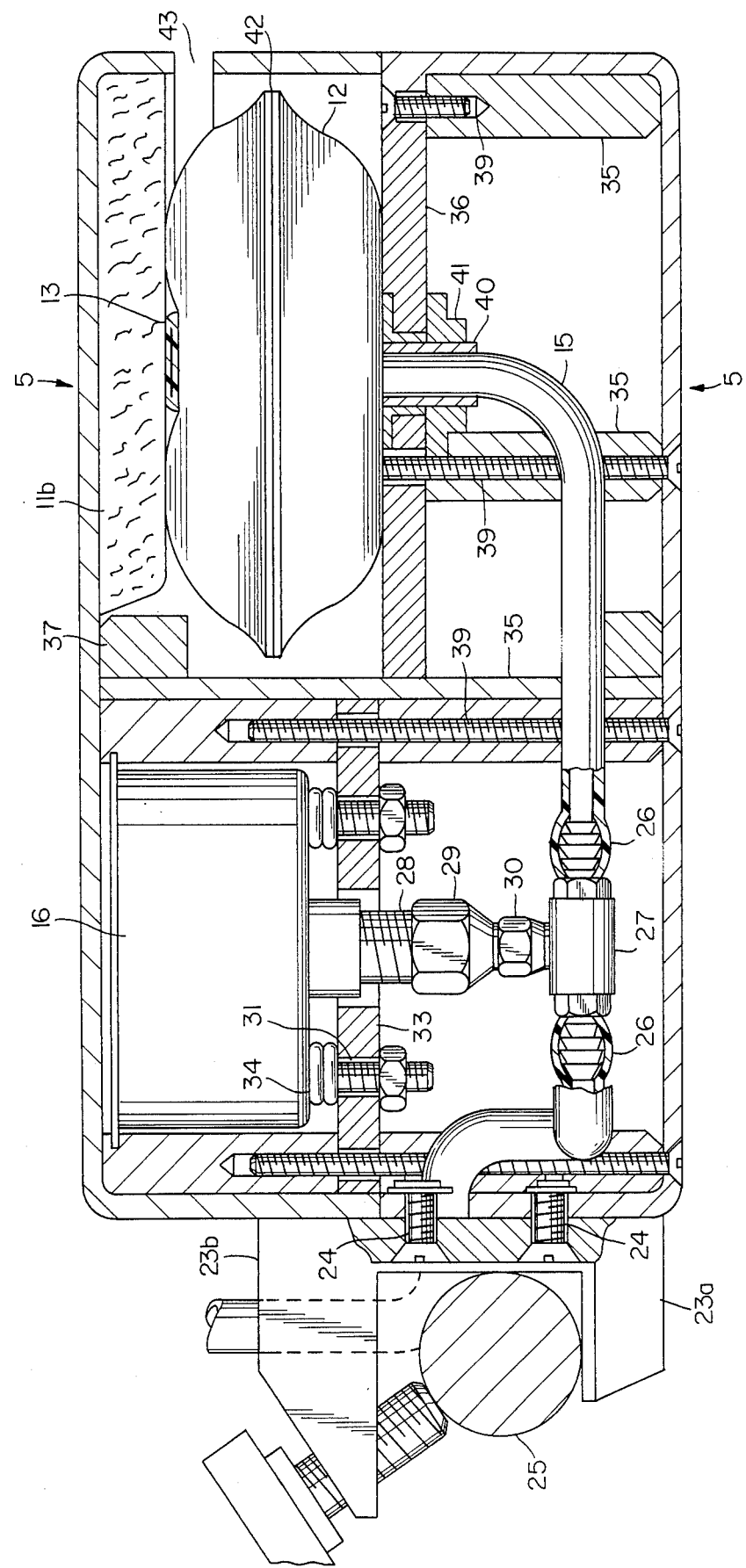

4,781,687

IRRIGATION SYSTEM UTILIZING AIR BLADDER PRESSURE REGULATOR AND METHOD OF USE

BACKGROUND OF THE INVENTION

Distention of a joint is often essential in an arthroscopic procedure. This is accomplished by introducing irrigation fluid under pressure into the joint to expand the joint so that it may be worked on more easily and to flush debris from the joint. Conventional techniques accomplish this by elevating a bottle of irrigation solution on a vertically adjustable intravenous infusion stand and connecting a fluid line to a catheter inserted into the joint. Pressure of the flud introduced to the joint can be increased or decreased by raising or lowering the irrigating solution reservoir on the vertically adjustable stand.

An improvement in the conventional technique is found in U.S. Pat. 4,604,089 which discloses a flow regulation circuit permitting an operator to actuate a first control to elevate the pressure in the irrigation site to a desired level and to maintain the pressure at that desired level when the first control is deactivated. Additionally, the operator may actuate a second control to reduce the pressure at the irrigation site to a base level determined by the height of the reservoir of the irrigation solution and to maintain the pressure at that reduced level when the second control is deactivated.

It would be desirable to have an apparatus which could be used to indirectly and non-invasively regulate and measure the pressure of the fluid in a joint without having to raise or lower a reservoir or operate an elaborate system of valves and flow circuits as disclosed in U.S. Pat. 4,604,089 to provide distention at a joint as well as to provide means for flushing debris from the joint cavity.

SUMMARY OF THE INVENTION

The present invention provides an apparatus and system for regulating the pressure at an irrigation site, such as in a joint capsule, without adjusting the height of the irrigation solution reservoir or operating an elaborate system of valves and circuits. The irrigation fluid is passed through the system and is not recirculated. The system for regulating pressure in a joint capsule includes catheters for providing fluid access to and egress from the irrigation site, the term "catheter" being used herein to mean any tubulature or device providing a passage for the flow of irrigating fluid to or from an operative site. When the catheter is introduced through the skin, the surrounding tissue tends to close around the exterior of the catheter to provide a seal. The system also includes any conventional pumping apparatus for pumping irrigation fluid into a circuit about the irrigation site. The fluid exits the irrigation site through an egress line which passes through a housing in which the tubing enlarges to form a bladder which has its outer surface in contact with an air bladder. The soft, flexible air bladder can be inflated by an operator to compress the soft, compliant flow-through egress bladder to substantially reduce or stop the fluid flow through the egress bladder. When the pressure in the egress bladder exceeds the pressure in the air bladder, the returning irrigation fluid displaces air from the air bladder and fluid flow increases in the egress line. The fluid flow releases pressure in the joint capsule and in the egress bladder. The pressure level, set by the air bladder and displayed on a pressure gauge, then returns to equilibrium. Further, the operator may release the pressure in the air bladder thereby allowing the egress bladder to expand and increase fluid flow and reduction of pressure at the irrigation site.

The pressure regulation apparatus permits an operator to distend the joint cavity for diagnostic and surgical procedures while flushing the joint capsule of debris.

When equilibrium is reached it not only provides control but accurate non-invasive pressure measurement in the joint capsule. It has been found that the pressure level in the flow through bladder and in an in vitro capsule followed the pressure level set in the air bag with ±10% accuracy in the 100–500 ml/min flow range. These parameters, however, are not intended to be limiting.

In an preferred embodiment, the air bladder may be inflated by hand using a simple bulb-type rubber pump. It may be deflated by adjusting a bleed valve adjacent to the rubber bulb pump. Therefore, only one hand is needed to regulate the joint capsule pressure in the irrigation system. An operator, merely by pumping the bulb to inflate the air bladder or turning the bleed valve to deflate the bladder can raise or lower the pressure at the irrigation site. Activation of the air bladder can be achieved by using fluid systems including mixtures of gas and liquid, instead of air. Further pressure levels can be set or controlled by automated pressure sources.

Thus, it is an object of the present invention to provide a simple irrigation system including a pressure regulation apparatus for use in irrigating body cavities and joints.

It is an object of the present invention to provide a simple irrigation system including a pressure regulation apparatus for use in arthroscopy.

A further object of the present invention is to provide a pressure regulation apparatus that contains an air bladder which can be inflated or deflated by simple manual manipulation.

A further object of the present invention is to provide means to regulate the pressure in a joint capsule to allow for distention of the joint capsule and removal of debris from the irrigation site.

Another object of the invention is to provide for a flow through egress bladder which is in continuous contact with an air bladder which maintains a pressure level in a joint capsule in accordance with the pressure level of the air bladder.

These and other features and advantages of the present invention will become apparent from the following detailed description of the preferred embodiments taken in conjunction with the following drawings.

BRIEF DESCRIPTION OF THE DRAWINGS

FIG. 4 is a sectional view of the apparatus taken at lines 4—4 of FIG. 3;

DETAILED DESCRIPTION OF THE PREFERRED EMBODIMENT

Figure 1:
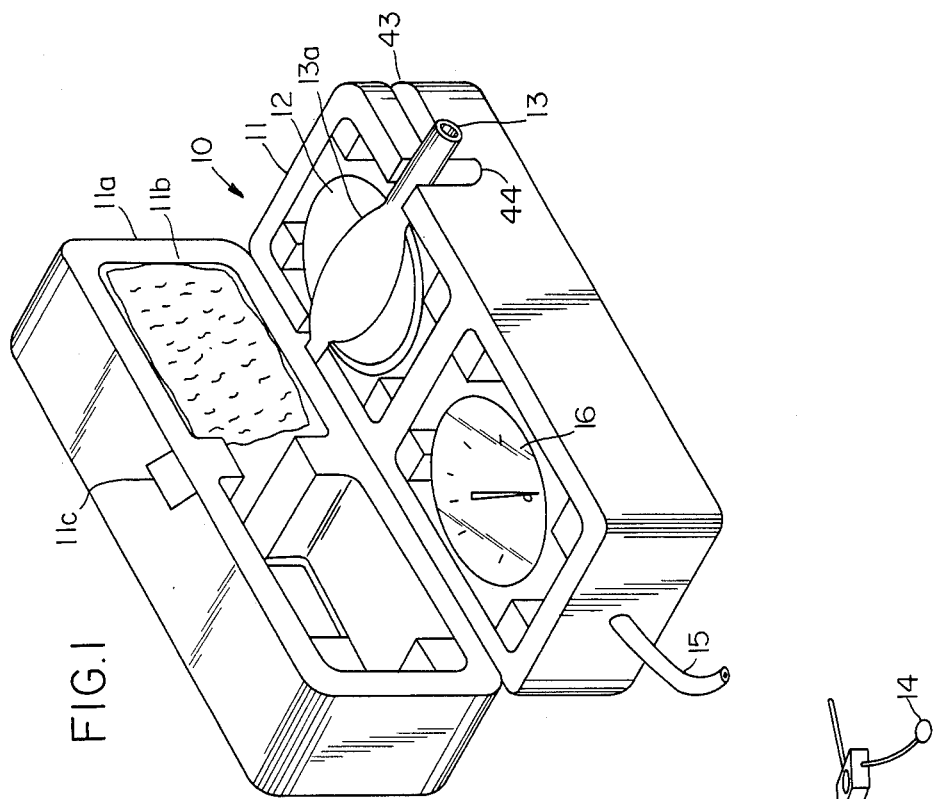
FIG. 1 is a perspective view of the pressure regulation apparatus of the present invention.

Referring to FIG. 1 there is shown the pressure regulation apparatus of the present invention generally designated 10 with housing base 11, and lid 11a in an opened position disclosing the contents therein. Housing 11 contains a cavity in which air bladder 12 is in contact with irrigation egress or outlet tubing 13 leading from an irrigation site and flow-through egress bladder 13a. Resilient material, such as elastomeric foam 11b within lid 11a contacts flow-through egress bladder 13a when lid 11a is closed and the egress bladder 13a is inflated. Locking mechanism 11c on lid 11a secures lid 11a to housing base 11.

Pump 14 is preferably a bulbous air pump operated by hand or foot. However, it may be an electrically operated air pump, or an automated pressure source. Line 15 transports air to bladder 12 via measuring instrument 16, which can be any suitable device for measuring air pressure. Gases other than air may be utilized in the air bladder 12 as well as liquid systems, including gas-air mixtures. The use of air in the present invention is not intended to be limiting.

Figure 3:
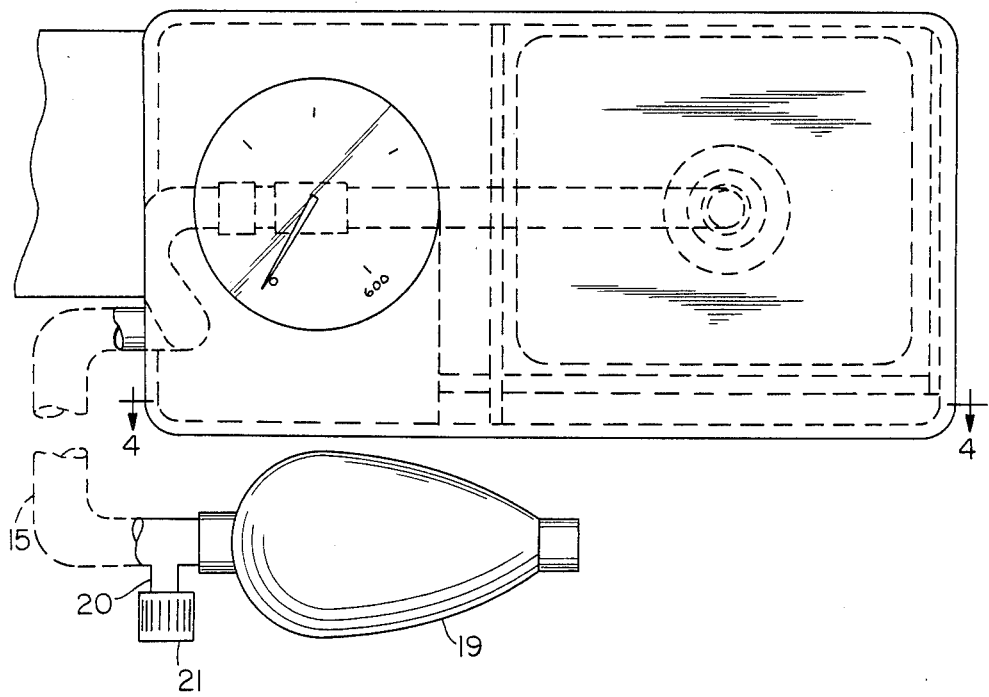
FIG. 3 is a top plan view of the pressure regulated apparatus.

With reference to FIG. 3, pump 14 is shown connected to line 15. Immediately adjacent oo pump 14 on line 15 is stem 20 which mounts knob 21 which can be manually adjusted to open or close a conventional bleed valve therein for releasing air from line 15.

FIG. 4 shows brackets 23a and 23b engage housing 11 by bolts 24. Line 15 passes under bracket 23a into housing 11. In this preferred assembly, bracket 23 may be secured to an intravenous infusion stand 25.

Connections 26 are provided in line 15 to connect valve 27 into line 15 for the passage of air to and from measuring instrument 16. Measuring instrument 16 monitors the air pressure passing through line 15 into bladder 12. Conduit 28 is secured to valve 27 by connections 29 and 30. Further, measuring instrument 16 is secured in housing 11 by bolts 31 and nuts 32 through housing support member 33. Springs 34 are interspaced around bolt 31 between the measuring instrument 16 and support member 33. Housing 11 contains transverse members 35 as well as additional support members 36 and 37 for securing air bladder 12.

Line 15 passes through transverse support members 35 which are secured by bolts 39 into housing 11 and enters air bladder 12 through rigid support means 40 and 41. Bolts 39 also secure support members 36 and 37 in housing 11.

Lines 15 and 13 are tubular conduits formed of resilient, flexible material having portions with enlarged cross-sections that have a flow passage of substantially greater cross-sectional area than found in the remainder of the conduit. The area comprising the enlarged cross-section is termed a bladder, i.e., air bladder 12 and flow-through egress bladder 13a. The term bladder is not intended to be limiting, however. Construction of the bladder, i.e., air bladder 12 or egress bladder 13a, may comprise one or two pieces of material and the bladders may be produced by any conventional procedure. The tubular conduits including collapsible bladder may be formed from any suitable, lightweight, resilient material, either elastomeric or non-elastomeric, or natural rubber, silicone, or woven material, such as impregnated Dacron cloth. The availability of tubing formed of non-elastomeric but resilient thermoplastic materials, such as polyvinyl chloride tubing commonly used in parental fluid administration sets, irrigation sets, and other delivery and drainage systems used in the medical field make such tubing highly desirable for use in the present invention for lines 13 and 15 and air bladder 12 and flow-through egress bladder 13a.

Figure 5:
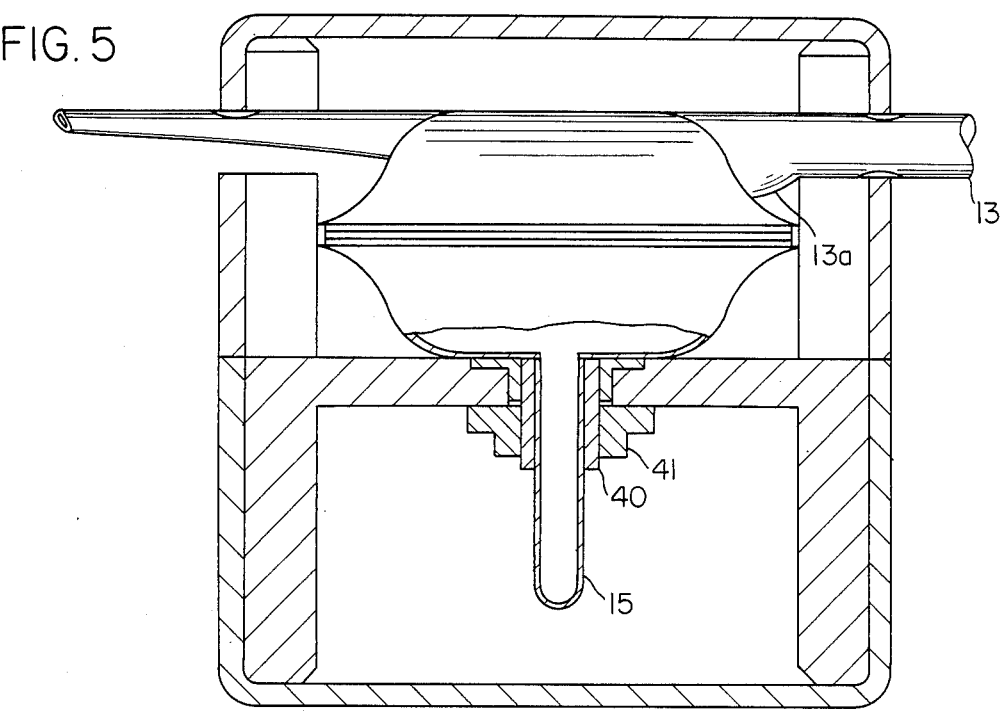
FIG. 5 is a sectional view of the apparatus taken at lines 5—5 of FIG. 4.

Air bladder 12 is shown in inflated condition in FIG. 5. Preferrably, the bladder may comprise two portions of lightweight material that may be sealed at the edges 42. The material utilized for constructing the bladder may be any lightweight material that has relatively good flexibility an must have the ability to be compressed completely flat by a low external pressure of about 10 mm Hg. There should be no bypass at the edges of the flattened bladder. Heat sealing or thermal forming of the edges is preferred. Excellent flexibility properties are needed so that the pressure inside bladder 12 can freely equilibrate with the pressure in flow through egress bladder 13a. A preferred material for air bladder 12 is polyvinyl chloride. Likewise, egress bladder 13 may be composed of a soft flexible material so that it may be easily compressed by air bladder 12. A preferred material is also polyvinyl chloride.

Within housing base 11 is slot 43 which is utilized for fitting egress bladder 13a in a contacting relationship with air bladder 12. As shown in FIG. 5 slot 43 is of a sufficient area to provide for the insertion and alignment of bladder 13a. Alternative slot 44, also within housing base 11 and perpendicular to slot 43 can also be utilized for the facile insertion of egress bladder 13a into housing base 11.

Figure 2:
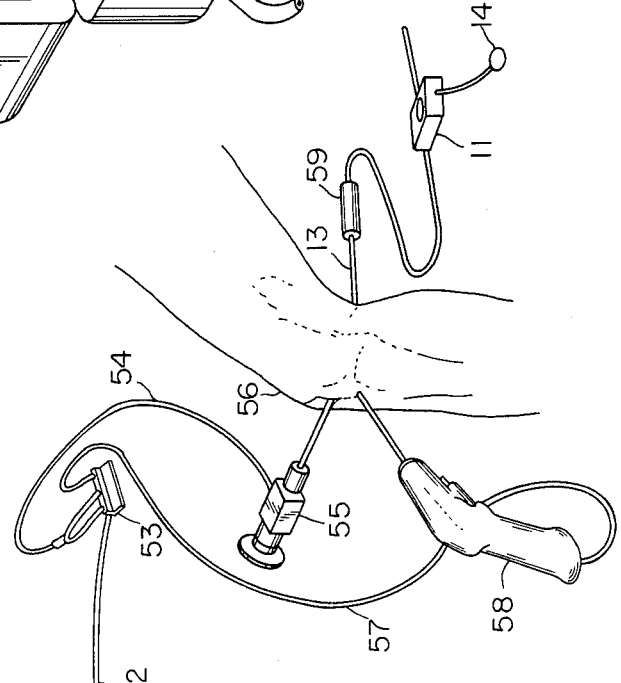
FIG. 2 is schematic view of the pressure regulated irrigation system of the present invention including a pump, access and egress catheters and the pressure regulation apparatus.

In operation, conventional pump 50 transports an irrigation fluid, normally a saline solution, from reservoir 51 through line 52 to manifold 53. There, access line 54 guides the fluid through catheter 55, as shown in FIG. 2, to knee 56, which is the irrigation site including the joint capsule. The present invention can be used with other joints and may also be used in areas of the body other than joints. An additional line 57 leads to surgical instrument 58. Egress line 13 carries fluid from the cavity through filter 59 to housing 11 of the pressure regulation apparatus of the present invention. The operator may restrict the flow of fluid in line 13 by manually manipulating pump 14 to inflate air bladder 12 so that it compresses egress bladder 13a within slot 43 in housing base 11. More importantly, the operator may control the pressure in the joint capsule by regulating the air pressure of air bladder 12. Once equilibrium of the air pressure in air bladder 12 and fluid pressure of joint capsule 13a is reached, the pressure in air bladder 12 is directly proportional to the fluid pressure in the joint capsule. Through the use of air bladder 12, fluid pressure in the joint capsule can be maintained regardless of the flow rate in egress tubing 13.

As the air pressure is increased in air bladder 12 by pumping bulb 14, flow through the egress bladder 13a is constricted so that the flow rate could drop to zero or at least be reduced. Simultaneously, irrigation fluid is being pumped into the joint capsule through access line 54 at a predetermined rate to distend the joint capsule. When the fluid pressure distends the joint capsule, the fluid pressure in line 13 causes egress bladder 13a to open and increase the corss-section of the fluid path. Fluid flow through the bladder 13a increases but the pressure equilibrium is maintained. Further, if the joint capsule needs to be flushed to remove blood or debris, the operator may simply release air into air bladder 12 to open egress bladder 13a to allow for increased fluid flow in the joint capsule to wash away the extraneous materials. When the irrigation fluid is clear, the air pressure in air bladder 12 may be restored. The manipulation of fluid and air pressure insures for the safe extension of the joint capsule without fear of injury to the joint or capsule membrane.

It will be appreciated that the present invention provides a pressure regulated system for an irrigation site and an apparatus for regulating pressure which permits the pressure to be quickly and easily elevated and maintained at the desired elevated level and then equally easily reduced and maintained at the reduced level without the necessity of raising and lowering an irrigation fluid reservoir on a traditional intravenous infusion stand. The present invention has been described in conjunction with perferred embodiments. Those skilled in the art will appreciate that many modifications and changes may be made to the preferred embodiments without departing from the present invention. It is, therefore, not intended to limit the present invention except as set forth in the apended claims.

What is claimed is:

1. A pressure regulation apparatus for irrigation system comprising:
    a housing defining a cavity,
    a fitting in said cavity for allowing the passage therethrough of an egress line from an irrigation site for carrying irrigation fluid,
    an egress bladder formed in said egress line in said cavity, said egress bladder having a greater cross-sectional area than said egress line,
    an air bladder in contact with said egress bladder in said cavity,
    means to inflate air bladder whereby an operator may increase the air pressure in said air bladder to restrict the flow in said egress bladder to increase the pressure at the irrigation site,
    further whereby an operator may decrease the air pressure in said inflated air bladder for increasing the flow in said egress bladder.

2. The apparatus of claim 1 wherein an inflated air bladder contacts effectively with the egress bladder to allow for the displacement of the air bladder when the pressure in the egress bladder exceeds the pressure in the air bladder.

3. The apparatus of claim 2 wherein the amount of fluid pressure in said egress bladder is proportional to the fluid pressure necessary to maintain distention or flushing at the irrigation site.

4. The apparatus of claim 2 wherein the amount of fluid pressure in said egress bladder is proportional to the pressure in the air bladder thereby regulating the distention or flushing of irrigation fluid at the irrigation site.

5. The apparatus of claim 2 wherein the egress bladder has fluid flow when the pressure in the air bladder is in a equilibrium state with the fluid pressure in the irrigation site.

6. The apparatus of claim 1 wherein said air bladder is inflated by an air pump or automated pressure source.

7. The apparatus of claim 1 including means to measure the air pressure within said air bladder.

8. The apparatus of claim 1 wherein the air bladder may contain gases other than air or liquid fluids or mixtures thereof.

9. A pressure regulated irrigation system comprising:
    means for providing access to and egress from the irrigation site,
    means for providing irrigation fluid to said access and egress means,
    an egress bladder formed in said egress means through which irrigation fluid flows from the irrigation site, said egress bladder having a greater cross-sectional area than said egress means,
    a bladder in contact with the egress bladder, said bladder being positioned to regulate the pressure in said egress bladder,
    means to inflate the bladder to restrict the flow in said egress bladder to increase pressure at the irrigation site, and,
    means to deflate the bladder in contact with the egress bladder thereby increasing the flow in said egress bladder and reducing pressure at the irrigation site.

10. The system of claim 9 wherein the inflated bladder contacts effectively with the egress bladder to allow for displacement of the inflated bladder when the pressure in the egress bladder exceeds the pressure in the inflated bladder.

11. The system of claim 9 wherein the bladder is inflated by air, gases other than air, liquid fluids and mixtures thereof.

12. The system of claim 9 wherein an operator may regulate pressure of the inflated bladder to be proportional to the fluid pressure at the irrigation site.

13. A method of regulating the pressure in an egress line of an irrigation system comprising:
    passing irrigation fluid from an irrigation site in a flexible, resilient egress line including a bladder formed therein, said bladder having a greater cross-sectional area than said egress line,
    contacting said egress bladder with a second inflated bladder that may regulate the pressure in said egress bladder, and
    inflating the second inflatable bladder to a level of pressure that can be displaced by pressure from said egress bladder so that an equilibrium of pressure is reached in said egress bladder, the second inflatable bladder and the irrigation site.

14. The method of claim 13 wherein the second inflated bladder is inflated by air, gases other than air, liquid fluids and mixtures thereof.

15. The method of claim 14 wherein the second inflated bladder is inflated to restrict the flow in said egress bladder to increase the pressure at the irrigation site.

16. The method of claim 14 wherein the second inflated bladder is deflated to increase the flow in said egress bladder.

* * * * *